(12) United States Patent
Nakano (10) Patent No.: US 9,284,150 B2
(45) Date of Patent: Mar. 15, 2016

(54) MEANDERING CORRECTION APPARATUS OF A CONTINUOUS SHEET ASSOCIATED WITH AN ABSORBENT ARTICLE

(75) Inventor: Takumi Nakano, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 551 days.

(21) Appl. No.: 13/809,633

(22) PCT Filed: Jul. 20, 2011

(86) PCT No.: PCT/JP2011/066396
§ 371 (c)(1),
(2), (4) Date: Mar. 18, 2013

(87) PCT Pub. No.: WO2012/014733
PCT Pub. Date: Feb. 2, 2012

(65) Prior Publication Data
US 2013/0175312 A1 Jul. 11, 2013

(30) Foreign Application Priority Data
Jul. 27, 2010 (JP) ................................ 2010-168363

(51) Int. Cl.
*B65H 23/032* (2006.01)
*A61F 13/15* (2006.01)
(Continued)

(52) U.S. Cl.
CPC ........ *B65H 23/032* (2013.01); *A61F 13/15772* (2013.01); *B65H 23/0216* (2013.01);
(Continued)

(58) Field of Classification Search
CPC ........... B65H 23/0204; B65H 23/0208; B65H 23/0216; B65H 23/0322; B65H 23/0324; B65H 23/032; B65H 2301/331; B65H 2301/3611; B65H 2301/36112; B65H 2553/81; B65H 2553/822; B65H 2553/82; B65H 2553/83; B65H 2553/41; B65H 2553/412; B65H 2553/414
See application file for complete search history.

(56) References Cited

U.S. PATENT DOCUMENTS 3,225,988 A * 12/1965 Drenning ........................ 226/19
4,848,632 A * 7/1989 Mack et al. ..................... 226/18
(Continued)

FOREIGN PATENT DOCUMENTS

| CN | 1460631 A | 12/2003 |
|---|---|---|
| CN | 201240679 Y | 5/2009 |

(Continued)

OTHER PUBLICATIONS

Extended European Search Report issued Nov. 7, 2014, corresponding to European patent application No. 11812325.6.
(Continued)

*Primary Examiner* — Michael McCullough
(74) *Attorney, Agent, or Firm* — Hauptman Ham, LLP (57) ABSTRACT

An apparatus for manufacturing absorbent articles includes: a detecting section detecting an edge position of a continuous sheet in the width direction when the detecting section is stopped at a stop position, a meandering correcting section correcting meandering of the continuous sheet, a motor moving the detecting section in the width direction, and a controller controlling the motor based on a movement signal related to movement of the detecting section. The controller has a value corresponding to a distance from a reference position to each stop position, moves the detecting section to each stop position based on the corresponding value and the movement signal. The controller detects that the detecting section reaches the reference position based on a current of the motor. The reference position is a limit position for physical movement in the width direction of the detecting section, and is at or outside the outermost stop position.

6 Claims, 8 Drawing Sheets

(51) Int. Cl.
*B65H 23/02* (2006.01)
*B65H 23/038* (2006.01)

(52) U.S. Cl.
CPC ..... *B65H23/038* (2013.01); *A61F 2013/15796* (2013.01); *B65H 2301/211* (2013.01); *B65H 2403/52* (2013.01); *B65H 2553/41* (2013.01); *B65H 2553/81* (2013.01); *B65H 2553/83* (2013.01); *B65H 2801/57* (2013.01)

(56) References Cited

U.S. PATENT DOCUMENTS

| | | | |
|---|---|---|---|
| 7,350,736 B2 * | 4/2008 | Caamano et al. | 242/390.9 |
| 2003/0213867 A1 | 11/2003 | Yomeoka | |
| 2010/0181007 A1 | 7/2010 | Yamamoto | |

FOREIGN PATENT DOCUMENTS

| | | |
|---|---|---|
| CN | 201343326 Y | 11/2009 |
| JP | 58-124907 A | 7/1983 |
| JP | 60-83110 A | 5/1985 |
| JP | 63-64586 A | 3/1988 |
| JP | 6-022682 Y2 | 6/1994 |
| JP | 11-139639 Y2 | 5/1999 |
| JP | 2004-043179 A | 2/2004 |
| JP | 2005-090212 A1 | 9/2005 |
| WO | 2005090212 A1 | 9/2005 |

OTHER PUBLICATIONS

International Search Report for PCT/JP2011/066396, dated Aug. 30, 2011.

Office Action dated Sep. 22, 2014, corresponding to Chinese patent application No. 201180036415.9.

* cited by examiner

FIG. 1

FIG. 2A SIDE VIEW

FIG. 2B VIEW ALONG ARROWS B-B

FIG. 2C VIEW ALONG ARROWS C-C

FIG. 3A  FOR SMALL SIZE

FIG. 3B  FOR MEDIUM SIZE

FIG. 3C  FOR LARGE SIZE

FIG. 3D  AT REFERENCE POSITION P0

FIG. 4A 
FOR MEDIUM SIZE

FIG. 4B 
AT REFERENCE POSITION P0

FIG. 4C 
FOR SMALL SIZE

MEANDERING CORRECTION APPARATUS OF A CONTINUOUS SHEET ASSOCIATED WITH AN ABSORBENT ARTICLE

RELATED APPLICATIONS

The present application is a National Phase of International Application Number PCT/JP2011/066396, filed Jul. 20, 2011, and claims priority from Japanese Application Number 2010-168363, filed Jul. 27, 2010.

TECHNICAL FIELD

The present invention relates to a meandering correction apparatus of a continuous sheet associated with an absorbent article such as a disposable diaper.

BACKGROUND ART

In a conventional manufacturing line of an absorbent article such as a disposable diaper, the absorbent article is manufactured, for example, by superposing and processing a plurality of continuous sheets.

In this manufacturing line, the continuous sheet is reeled out from a whole cloth roll and continuously transported in the transporting direction. At the time of this transport, there is a risk that the continuous sheet will meander. Therefore, a meandering correction apparatuses is arranged at each of the appropriate positions of the transport path. With these apparatuses, for example, the position of the continuous sheet in the width direction is corrected so that the central position of the continuous sheet in the width direction corresponds with the central position of the manufacturing line in the width direction of the line.

The meandering correction apparatus includes a roll around which the continuous sheet is disposed, for example. Then, based on a detection signal from an edge sensor that detects a position of an edge of the continuous sheet in the width direction, the meandering of the continuous sheet in the width direction is corrected by oscillating the roll.

The edge sensor includes a sensor head that has a detecting section such as a phototube, and this sensor head is stopped at a predetermined stop position in the width direction. In the stopped state, the sensor head detects a change in the light shielding condition that changes along with the shifting of the edge position of the continuous sheet in the width direction which is detected based on the changes in the amount of received light by the detecting section. In this manner, the position of the edge of the continuous sheet is detected (Patent Literature 1).

CITATION LIST

Patent Literature

[PTL 1]
Japanese Translation of PCT International Application No. 2005-090212

SUMMARY OF THE INVENTION

Technical Problem

In the manufacturing line of the absorbent article, a plurality of absorbent articles having different size specifications is manufactured. For example, the absorbent articles in each size of Small, Medium, and Large are manufactured. Therefore, the above-mentioned stop position is also prepared in accordance with each size of Small, Medium, and Large. The sensor head is moved to each stop position corresponding to the size of the absorbent article to be manufactured each time the size is changed.

A moving mechanism that moves this sensor head includes a motor that moves the sensor head in the width direction, an encoder that generates a pulse signal in accordance with the movement of the sensor head, and a controller that controls the motor based on the signal. The controller counts the number of pulses of the signal based on the reference position set at the predetermined position in the width direction. When the count value reaches a predetermined value, the controller determines that the sensor head has reached the target stop position, and stops the motor. More specifically, when the size is changed, the sensor head is once moved to the reference position and then moved from the reference position to the target stop position.

Here, the reaching of the sensor head to the reference position is generally detected by using a position detecting switch such as a limit switch or a proximity switch. That is, this kind of position detecting switch is arranged at the reference position, and the controller receives the output signal from the position detecting switch to determine whether the sensor head has reached the reference position or not.

However, the meandering correction apparatus is provided at a plurality of positions along the transport path as mentioned above. Therefore, it is also necessary to provide a plurality of the above-mentioned position detecting switches associated with the reference position, and when these position detecting switches are provided, the equipment will become complicated. For example, since a plurality of signal cables for output signals have to be routed from the position detecting switches to the controller, these signal cables will be entangled making the equipment intricate.

Moreover, in the case that the above-mentioned reference position is present inside the edge of the continuous sheet in the width direction of the sheet, each time the sensor head is moved to the reference position when changing the size, the sensor head interferes with the continuous sheet. Therefore, the sensor head cannot reach the reference position, or the continuous sheet will be deformed.

The present invention has been made in view of the conventional problems described above, and an advantage thereof is to simplify the configuration of the meandering correction apparatus, and to avoid interference between the continuous sheet and the detecting section associated with the sensor head when the specifications of the absorbent article are changed, for example, when the size is changed.

Solution to Problem

A principal aspect of the invention for achieving the above advantage is a meandering correction apparatus of a continuous sheet associated with an absorbent article, that is arranged in a manufacturing line of the absorbent article and corrects meandering of the continuous sheet being continuously transported in a transporting direction, in which a continuous sheet having one specification is selected, to be transported, from among a plurality of continuous sheets each having a specification with a dimension in a width direction different from each other, including:

a sensor including a detecting section that detects a position of an edge of the continuous sheet in the width direction and detecting the position of the edge in a state in which the detecting section is stopped at a stop position set in the width direction for each of the specifications, a meandering correcting section that corrects meandering of the continuous sheet based on a detection signal of the position of the edge which is output from the sensor, and a moving mechanism moving the detecting section to the stop position, the moving mechanism including a motor that moves the detecting section in the width direction, a signal output section that outputs a signal in accordance with the movement of the detecting section in the width direction, and a controller that controls the motor based on the signal, the controller having a corresponding value that corresponds to a moving distance from a predetermined reference position to the stop position as a predetermined value for each stop position, the controller moving the detecting section to the stop position based on the corresponding value and the signal output from the signal output section, the reference position being a limit position for physical movement associated with the width direction of the detecting section, the controller detecting that the detecting section reaches the reference position based on a drive current value of the motor, and the reference position being located at a same position as a stop position located at an outermost position in the width direction among the stop positions, or being located outside of the outermost stop position.

Other features of this invention will become apparent from the description in this specification and the attached drawings.

Effects of the Invention

According to the present invention, it is possible to simplify the configuration of the meandering correction apparatus, and to avoid the continuous sheet from interfering with the detecting section associated with the sensor head when the specification of the absorbent article is changed, for example, when the size is changed.

MODE FOR CARRYING OUT THE INVENTION

At least the following matters will be made clear by the description in the present specification and the accompanying drawings.

A meandering correction apparatus of a continuous sheet associated with an absorbent article, that is arranged in a manufacturing line of the absorbent article and corrects meandering of the continuous sheet being continuously transported in a transporting direction, in which a continuous sheet having one specification is selected, to be transported, from among a plurality of continuous sheets each having a specification with a dimension in a width direction different from each other, including:

a sensor including a detecting section that detects a position of an edge of the continuous sheet in the width direction and detecting the position of the edge in a state in which the detecting section is stopped at a stop position set in the width direction for each of the specifications, a meandering correcting section that corrects meandering of the continuous sheet based on a detection signal of the position of the edge which is output from the sensor, and a moving mechanism moving the detecting section to the stop position, the moving mechanism including a motor that moves the detecting section in the width direction, a signal output section that outputs a signal in accordance with the movement of the detecting section in the width direction, and a controller that controls the motor based on the signal, the controller having a corresponding value that corresponds to a moving distance from a predetermined reference position to the stop position as a predetermined value for each stop position, the controller moving the detecting section to the stop position based on the corresponding value and the signal output from the signal output section, the reference position being a limit position for physical movement associated with the width direction of the detecting section, the controller detecting that the detecting section reaches the reference position based on a drive current value of the motor, and the reference position being located at a same position as a stop position located at an outermost position in the width direction among the stop positions, or being located outside of the outermost stop position.

With such a meandering correction apparatus, the reaching of the detecting section to the reference position is detected by a drive current value of the motor. Accordingly, it is not necessary to provide a position detecting switch such as a limit switch or a proximity switch at the reference position, and the configuration of the apparatus can be simplified.

Further, since the reference position is located at the same position as the stop position located at the outermost position in the width direction, or is located outside the outermost stop position, the reference position is located outside the continuous sheet in the width direction. Accordingly, when the specification is changed, it is possible to effectively avoid interferences such as the detecting section contacting the continuous sheet during the movement of the detecting section toward the reference position.

In such a meandering correction apparatus of a continuous sheet associated with an absorbent article, it is desirable that the detecting sections are arranged one each on two sides in the width direction.

With such a meandering correction apparatus, the position of the edges of the continuous sheet in the width direction of the sheet can be detected. Accordingly, by using these two detecting sections, even if the dimension of the continuous sheet in the width direction in the same continuous sheet is varied, the central position of the continuous sheet in the width direction can be accurately recognized. As a result, the meandering can be surely corrected without being affected by the varying of the dimension in the width direction.

In such a meandering correction apparatus of a continuous sheet associated with an absorbent article, it is desirable that the moving mechanism is provided to each of the detecting sections on the two sides, and the reference position and the stop position are set to the each detecting section.

With such a meandering correction apparatus, since the moving mechanism, the reference position and the stop position are provided for each detecting section, each of the detecting sections is moved to the stop position independent of each other for each detecting section. Accordingly, each detecting section can be accurately positioned at the stop position to be stopped based on the reference position corresponding to each of the detecting sections.

In such a meandering correction apparatus of a continuous sheet associated with an absorbent article, it is desirable that the meandering correction apparatus is supported by a plate member standing vertically at one side of the width direction, and the sensor is provided only at another side in the width direction.

With such a meandering correction apparatus, the sensor is arranged at the side away from the plate member in the width direction. Accordingly, the panel member will not interfere with the sensor when performing maintenance and inspection thereof, and excellent maintainability can be achieved.

In such a meandering correction apparatus of a continuous sheet associated with an absorbent article, it is desirable that the reference position is a position same as the stop position located at the outermost position.

With such a meandering correction apparatus, if the stop position where the detecting section is to be stopped next is the outermost stop position when changing the specification, the detecting section can be positioned at the stop position without moving from the reference position. Accordingly, it is possible to avoid influences of errors occurring along with the movement from the reference position to the stop position, so that the detecting section can be accurately positioned at the stop position.

Present Embodiment

Figure 1:
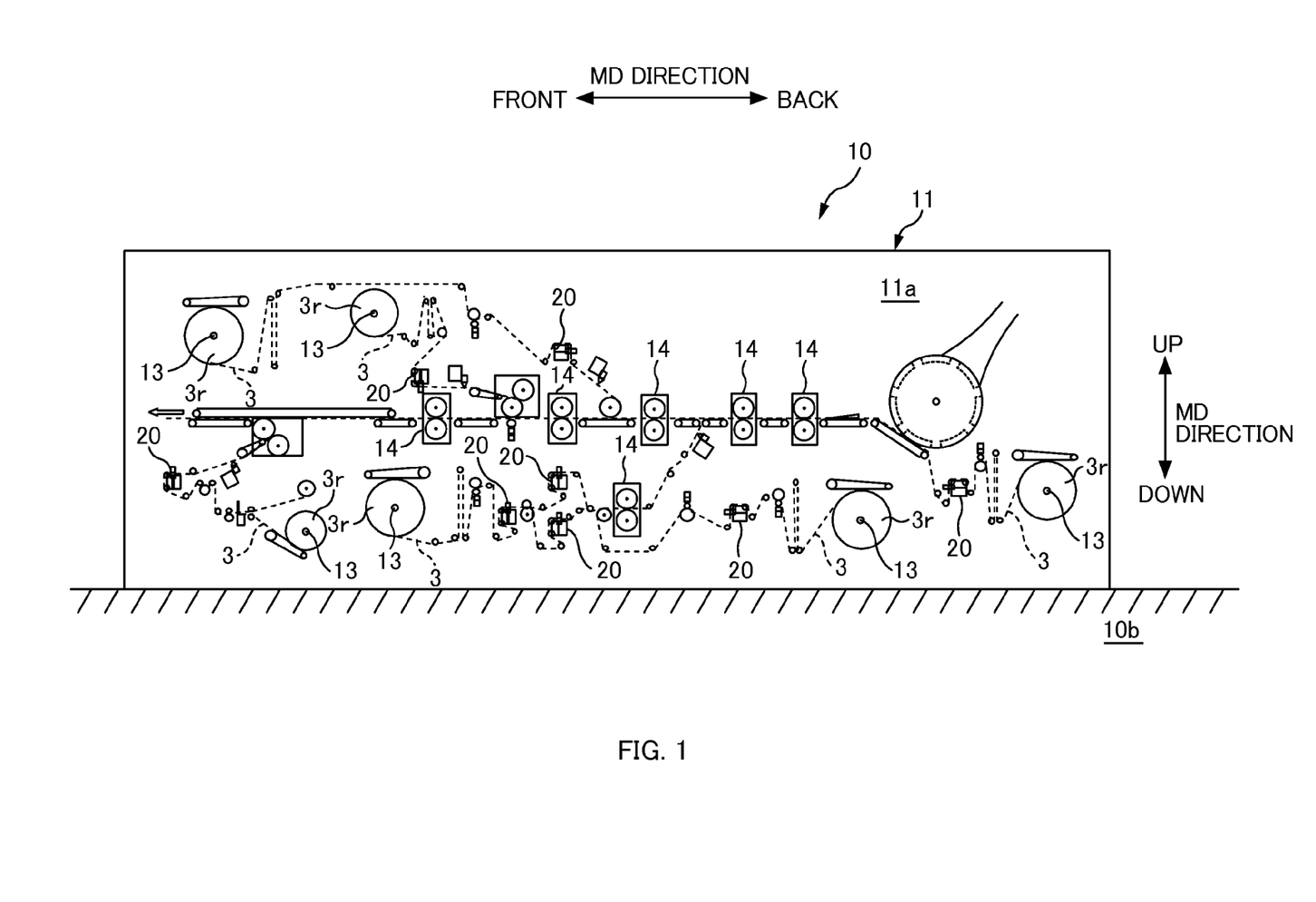
FIG. 1 is a schematic side view of a manufacturing line 10 of an absorbent article.

FIG. 1 is a schematic side view of a manufacturing line 10 of an absorbent article.

In manufacturing the absorbent article, a plurality of continuous sheets 3, 3 . . . is used as the material thereof. For example, a fibrous continuous sheet 3 having pliability and flexibility such as nonwoven fabric, woven fabric, or tissue paper is used. Delivering such continuous sheets 3, 3 . . . into the manufacturing line 10 is performed in the form of the sheet rolls 3r, 3r . . . (the continuous sheet 3 wound up into a roll (whole cloth roll)). Each sheet roll 3r is mounted to an appropriate reel device 13, and each continuous sheet 3 is reeled out in the transporting direction. While being transported along the predetermined transport path in the manufacturing line 10 (seethe dotted lines in FIG. 1), each continuous sheet 3 is such as pressed and cut by various processing units 14, 14 . . . , and then is superposed or the like with another continuous sheet 3. And finally, an absorbent article is manufactured.

In the following description, the width direction of the manufacturing line 10 (a direction perpendicular to the paper surface in FIG. 1) is referred to as the "CD direction", and any direction in the plane perpendicular to the CD direction is referred to as the "MD direction". The CD direction is directed in a horizontal direction, and this direction is also referred to as a "left-and-right direction". Also, in the two directions which are perpendicular to each other in the MD direction, the vertical direction is referred to as the "up-and-down direction", and the horizontal direction is referred to as the "front-and-back direction".

More specifically, when the continuous sheet 3 is correctly transported without meandering, the transporting direction of the continuous sheet 3 is parallel to the MD direction, and the width direction of the continuous sheet 3 is parallel to the CD direction.

During transportation in this manufacturing line 10, there is a risk that the continuous sheet 3 will meander. That is, there are cases in which the central position in the CD direction of the continuous sheet 3 is displaced from the central position in the CD direction of the manufacturing line 10, which is the target position. Therefore, in the transport path of the continuous sheet 3, meandering correction apparatuses 20 are appropriately arranged. Note that in the following description, one meandering correction apparatus 20 will be described, however, at least one or more meandering correction apparatuses 20 having a similar configuration thereto are arranged for each continuous sheets 3, 3 . . . .

In the same manufacturing line 10, absorbent articles of a plurality of specifications are manufactured. For example, the absorbent article in this example is manufactured in three sizes of Small, Medium, and Large as an example of the plurality of specifications. Accordingly, in the manufacturing line 10, the product size is changed at regular intervals, and due to this, the size of the continuous sheet 3 that passes through the meandering correction apparatus 20 is also changed. More specifically, one continuous sheet 3 is selected from among continuous sheets 3S, 3M, 3L with three different widths of Small, Medium, and Large, respectively, and is passed through the meandering correction apparatus 20 (see FIGS. 3A to 3C).

Figure 2A:
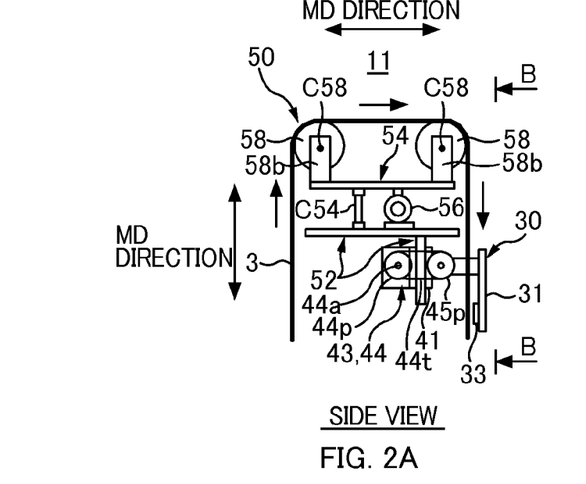
FIG. 2A is a schematic side view of a meandering correction apparatus 20.
Figure 2B:
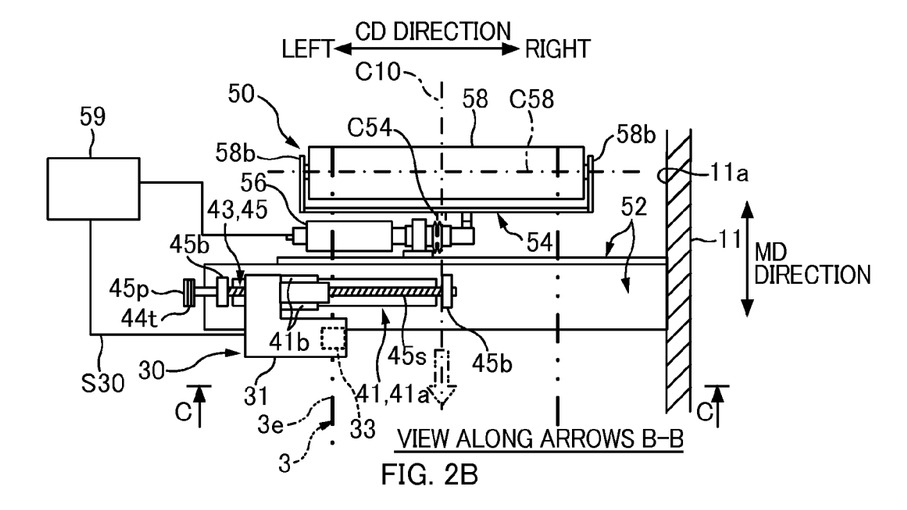
FIG. 2B is a view along arrows B-B in FIG. 2A.
Figure 2C:
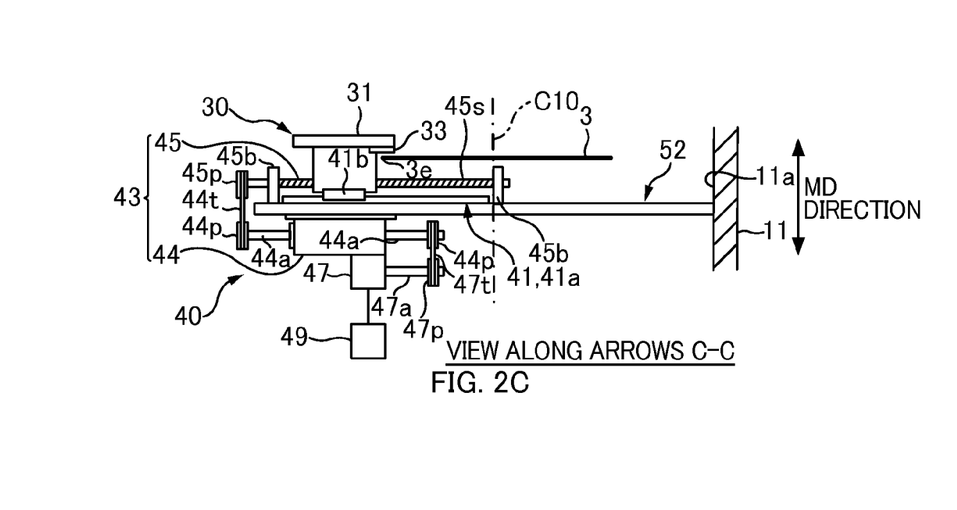
FIG. 2C is a view along arrows C-C in FIG. 2B.

FIGS. 2A to 2C are explanatory views of the meandering correction apparatus 20 of the continuous sheet 3 of the present embodiment. FIG. 2A is a schematic side view of the meandering correction apparatus 20, FIG. 2B is a view along arrows B-B in FIG. 2A, and FIG. 2C is a view along arrows C-C in FIG. 2B.

The meandering correction apparatus 20 is supported by a panel board 11 of the manufacturing line 10 in a cantilevered manner, for example. Here, as shown in FIG. 1, the panel board 11 is a plate member standing vertically on a foundation 10b of the manufacturing line 10 in order to support various devices 14, 14 . . . of the manufacturing line 10. More specifically, the panel board 11 is arranged by extending in the up-and-down direction and the front-and-back direction which are the MD directions, at one side (for example, right side) of the CD direction of the manufacturing line 10. The various devices 14, 14 . . . are supported substantially in a cantilevered manner by using each vertical surface 11a as a support surface.

The meandering correction apparatus 20 includes an edge sensor 30 (corresponding to the sensor) that detects a position of an edge 3e of the continuous sheet 3 in the width direction of the sheet, and a meandering correcting section 50 that corrects the meandering of the continuous sheet 3 based on a detection signal S30 indicating a position of the edge 3e, which is output from the edge sensor 30.

The meandering correcting section 50 includes a fixed pedestal 52 supported by the panel board 11 in a cantilevered manner. In this fixed pedestal 52, an oscillating platform 54 is supported around a predetermined fixed shaft C54 so as to freely oscillate, and an oil hydraulic cylinder 56 is provided as a drive source for oscillating the oscillating platform 54. In addition, in the oscillating platform 54, a pair of transport rolls 58, 58 that are aligned adjacent and parallel to each other in the MD direction are rotatably supported around each shaft core C58 by bearing members 58b, 58b. Further, the continuous sheet 3 is spread across the pair of transport rolls 58, 58 at a predetermined wrapping angle such as 90 degrees, so that the transporting direction of the continuous sheet 3 is reversed substantially 180 degrees. Therefore, the continuous sheet 3 is restricted by the pair of transport rolls 58, 58 in a U-shaped form when viewed from the side. Thus, due to the above-mentioned oscillating movement, if the rotational direction of these transport rolls 58, 58 is oriented to the direction inclined from the MD direction, the position of the continuous sheet 3 as a whole can be shifted to the CD direction.

On the other hand, the meandering correcting section 50 also includes a first controller 59 such as an appropriate computer or sequencer. In the first controller 59, the detection signal S30 indicating the position of the edge 3e of the continuous sheet 3 is input from the above-mentioned edge sensor 30. Accordingly, the first controller 59 corrects the meandering of the continuous sheet 3 by controlling the oil hydraulic cylinder 56 based on the detection signal S30.

The edge sensor 30 is arranged at a downstream position most proximate the meandering correcting section 50 in the MD direction, and is supported on the above-mentioned fixed pedestal 52. The edge sensor 30 includes a sensor head 31 having a detecting section 33 that detects a position of the edge 3e of the continuous sheet 3, and a moving mechanism 40 that moves the sensor head 31 in the CD direction.

Figure 3A:
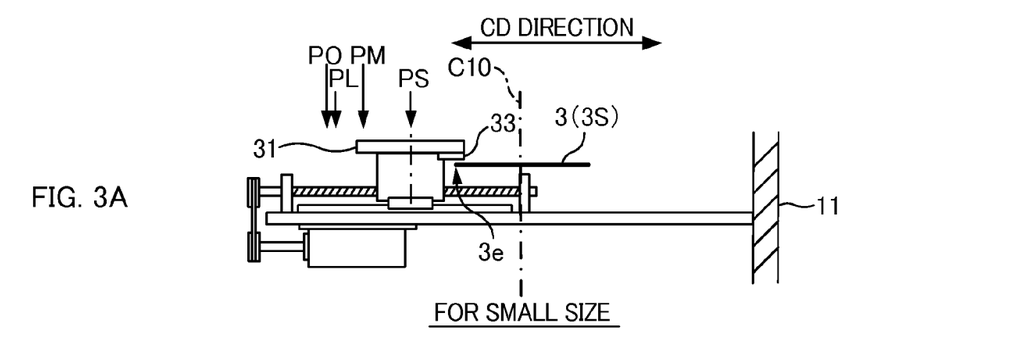
FIG. 3A is an explanatory view of a stop position PS for Small size.
Figure 3B:
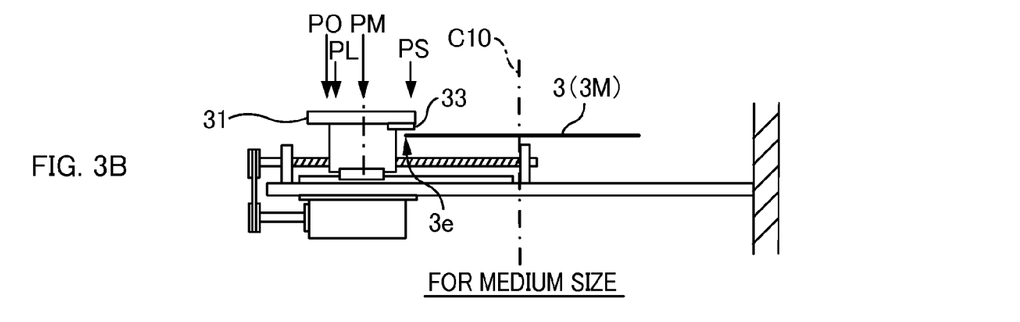
FIG. 3B is an explanatory view of a stop position PM for Medium size.
Figure 3C:
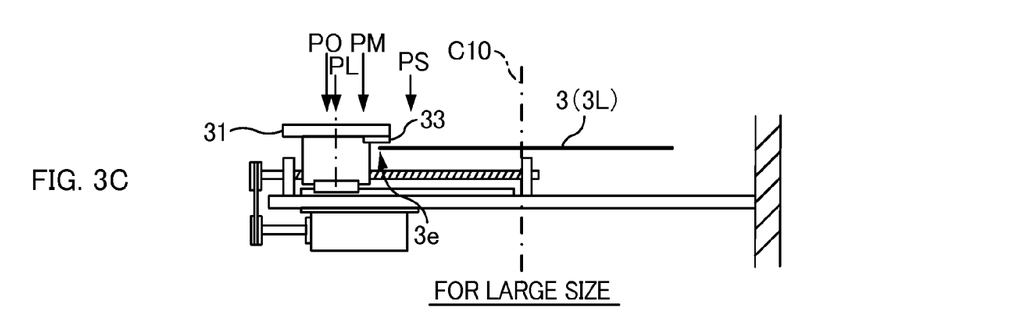
FIG. 3C is an explanatory view of a stop position PL, for Large size.

Here, as shown in FIGS. 3A to 3C, stop positions PS, PM, PL at which the sensor head 31 is to be stopped are set in the CD direction. Such stop positions PS, PM, PL are set for each specification of the absorbent article that is to be manufactured in this manufacturing line 10. In this example, since the specification corresponds to the product sizes, the stop position PS for Small size, the stop position PM for Medium size, and the stop position PL for Large size products are sequentially set from the inner side in the CD direction toward the outer side thereof. The detecting section 33 of the sensor head 31 is moved to the stop position PS, PM, or PL that corresponds to the product size to be manufactured, and then detects the position of the edge 3e of the continuous sheet 3 in a state stopped at that position.

The detecting section 33 has, for example, a phototube as its main body. The phototube generates an electrical signal whose magnitude is substantially proportional to the amount of received light. The amount of received light changes depending on the condition of the light blocked by the edge 3e of the continuous sheet 3 in the width direction of the sheet. Then, the above electrical signal is converted to a signal indicating a position in the CD direction by an operation section (not shown) in the detecting section 33, and this signal is output to the first controller 59 as a detection signal S30 of the position of the edge 3e of the continuous sheet 3. Note that, although the phototube is used in this example, the main body is not limited to a phototube.

As shown in FIGS. 2A to 2C, the moving mechanism 40 that moves the sensor head 31 includes a guide member 41 that guides the movement of the sensor head 31 in the CD direction, a drive mechanism 43 that moves the sensor head 31 in the CD direction, a rotary encoder 47 as a signal output section that outputs a signal in accordance with the movement of the sensor head 31, and a second controller 49 (corresponding to the controller) that controls the drive mechanism 43 based on the signal output from the rotary encoder 47.

The guide member 41 is, for example, a linear guide. More specifically, the guide member 41 includes a rail 41a arranged along the CD direction on the fixed pedestal 52, and sliders 41b, 41b that are slidably engaged with this rail 41a. The sensor head 31 is fixed to the sliders 41b, 41b by bolting or the like. Thereby, the sensor head 31 is movably guided in the CD direction.

The drive mechanism 43 includes a motor 44 and a feed screw mechanism 45. The feed screw mechanism 45 converts a rotating motion of a drive rotational shaft 44a of the motor 44 to a linear movement in the CD direction to be transmit to the sensor head 31. Here, a ball screw mechanism 45 is used as the feed screw mechanism 45. That is, a screw shaft 45s of the ball screw mechanism 45 is arranged so that the axial direction thereof comes along the CD direction. In this state, the screw shaft 45s is rotatably supported by bearing members 45b, 45b at both end portions thereof. Also, in a helical groove of the outer circumferential surface of the screw shaft 45s, a nut member (not shown) is screwed via ball-shaped rolling elements (not shown), and the sensor head 31 is fixed to this nut member. Further, a drive rotational shaft 44a of the motor 44 and the screw shaft 45s are connected by a rotating motion transmitting member such as pulleys 44p, 45p, or a timing belt 44t. Therefore, when the rotating motion of the drive rotational shaft 44a of the motor 44 is transmitted to the screw shaft 45s to rotate the screw shaft 45s, the sensor head 31 is moved in the CD direction in an integrated manner with the nut member.

The rotary encoder 47 includes, for example, an input shaft 47a, and generates the number of pulses which is proportional to the amount of rotation input to the input shaft 47a. Also, this input shaft 47a is connected to the drive rotational shaft 44a of the motor 44 by the pulleys 47p, 44p and the timing belt 47t. Accordingly, the encoder 47 generates the number of pulses corresponding to the amount of rotation of the drive rotational shaft 44a. Then, the signal having such pulses is output to the second controller 49.

Figure 3D:
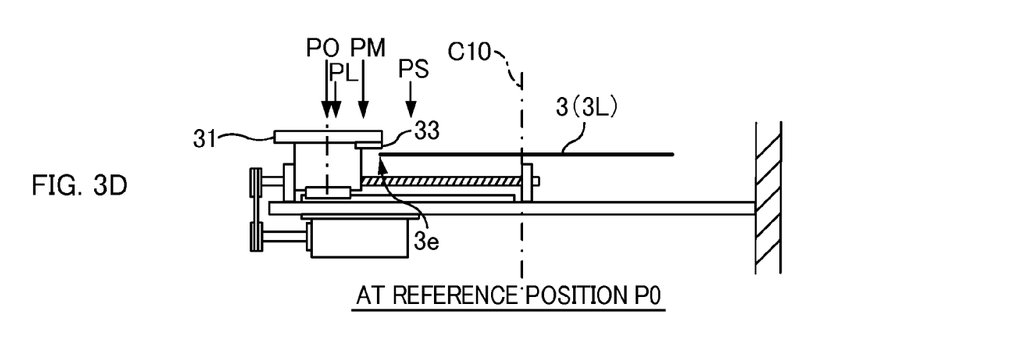
FIG. 3D is an explanatory view of a reference position P0.

The second controller 49 is also an appropriate computer or sequencer, and includes a counter circuit that counts the pulses. As shown in FIG. 3D, this counter circuit is configured so as to perform a zero-reset of the count value of the pulse when the sensor head 31 has reached the predetermined reference position P0 set in the CD direction. Furthermore, in a memory of the second controller 49, each corresponding value that corresponds to a distance moved from the reference position P0 to each stop position PS, PM, and PL, is recorded in advance for each stop position PS, PM, and PL in the form of count values.

Figure 4A:
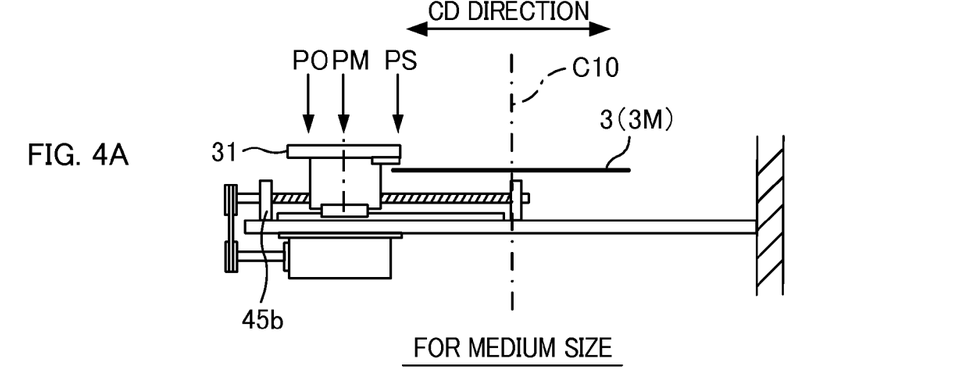
FIGS. 4A to 4C are explanatory views of an example of the size change, and show how the size is changed from Medium size to Small size.
Figure 4B:
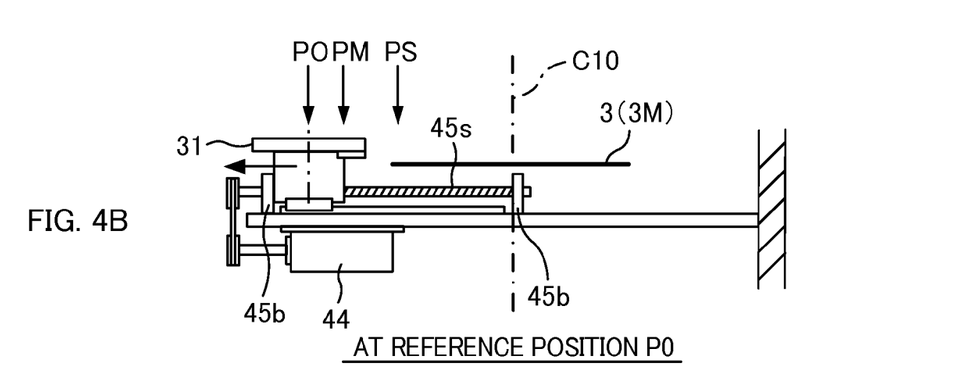
Figure 4C:
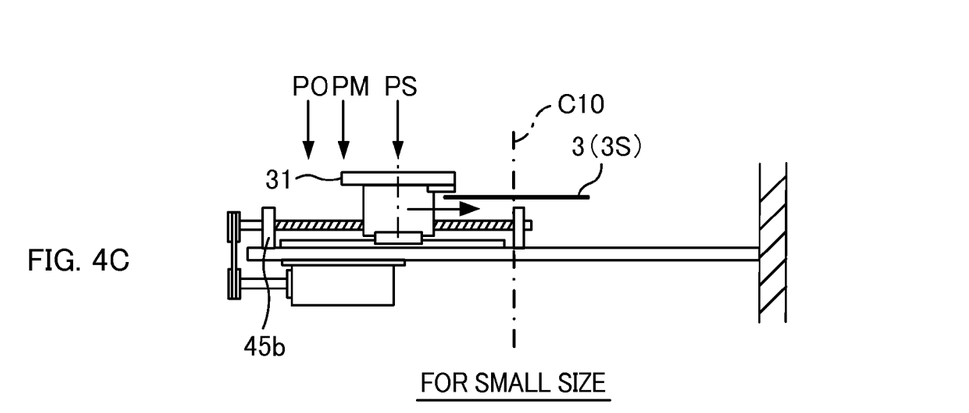
Figure 5:
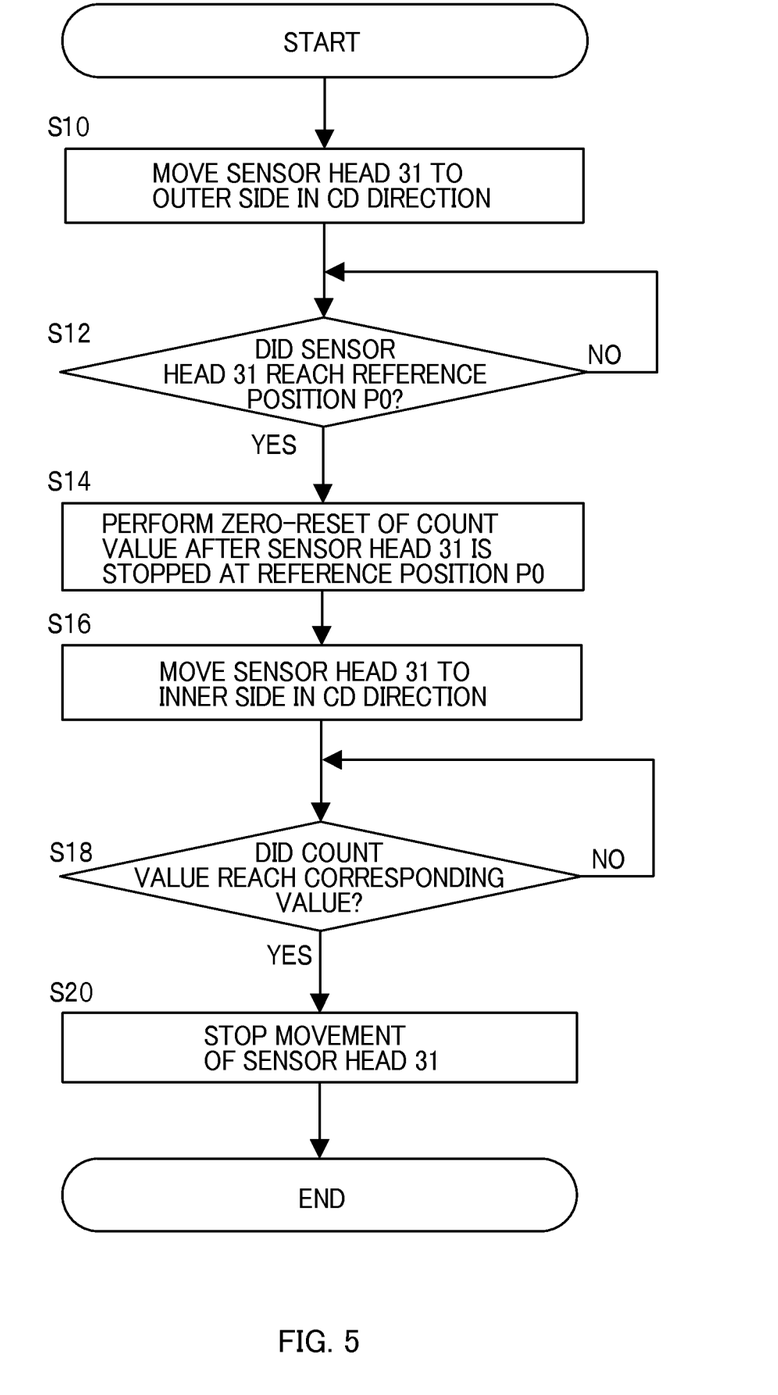
FIG. 5 is a flowchart of a processing performed by a second controller 49 when the size is changed.

Accordingly, for example, when the product size is changed from Medium size to Small size, the second controller 49 first moves the sensor head 31 to the outer side in the CD direction (step S10, hereinafter, refer to the flowchart of FIG. 5 for each step according to need) as shown in FIGS. 4A and 4B, and performs a zero-reset of the count value when the sensor head reaches the reference position P0 (steps S12, and S14). Then, the sensor head 31 is moved to the inner side in one direction along the CD direction while making the counter circuit count therefrom (step S16). When the count value reaches the corresponding value that corresponds to the stop position PS for the next product size, as shown in FIG. 4C, the motor 44 is stopped in order to stop the movement of the sensor head 31 (steps S18, and S20). Thereby, the position of the sensor head 31 is adjusted to the stop position PS. Such operation is performed when changing to other sizes as well.

In the present embodiment, the above-mentioned reference position P0 is set to a limit position for physical movement of the sensor head 31. This "limit position for physical movement" is a position where the sensor head 31 abuts an interfering object or the like when moving in the CD direction.

As an example of the interfering object, there are the above-mentioned bearing member 45*b* that supports the screw shaft 45*s* at the end portions thereof, an edge of the helical groove of the screw shaft 45*s*, and the like. In the present embodiment, as shown in FIG. 4B, the former is applied. That is, the above-mentioned reference position P0 is set at the position where the sensor head 31 abuts the outer side bearing member 45*b* in the CD direction of a pair of bearing members 45*b*, 45*b* arranged in the CD direction. Then, the sensor head 31 abuts the outer side bearing member 45*b*, so that the sensor head 31 is restricted in a state in which any further movement toward the outside is ceased. When the latter edge of the helical groove of the latter screw shaft 45*s* is used as the interfering object, the rolling elements of the nut member reaches the above-mentioned edge making it impossible for the rolling elements to roll any further. Thereby, it becomes impossible for the sensor head 31 to move any further to the outer side.

When the sensor head 31 reaches such reference position P0, a driving torque (rotational resistance) required for the movement of the sensor head 31 becomes excessive. Due to this, the drive current value of the motor 44 abruptly increases, and with this the reaching of the sensor head 31 to the reference position P0 is detected in the present embodiment.

Figure 6:
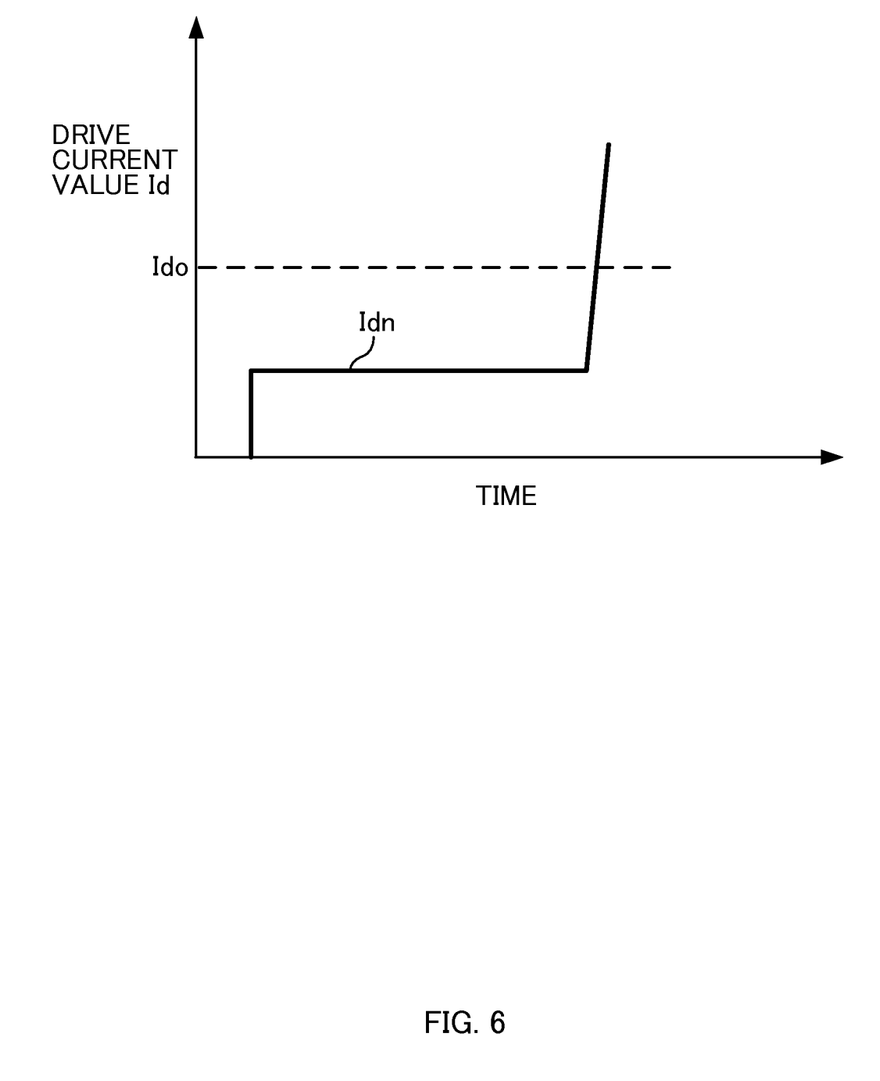
FIG. 6 is a chart of a drive current Id used for detecting that a sensor head 31 has reached the reference position P0.

More specifically, the drive current Id of the motor 44 is measured at all times by a galvanometer (not shown), and when the measurement value thereof exceeds a predetermined threshold Id0 as shown in FIG. 6, the sensor head 31 is determined to have reached the reference position P0. With such a configuration, there is no need to provide a limit switch, a proximity switch or the like at the reference position P0, so that a simplified apparatus configuration can be achieved.

Furthermore, by using particularly a servomotor as the motor 44, since the servomotor generally includes a galvanometer and an output terminal thereof, the measurement value of the drive current Id of the motor can be easily output to the second controller 49.

The above-mentioned threshold Id0 associated with the reference position P0 shown in FIG. 6 is set to a higher value than the maximum value of a stationary value Idn in comparing the stationary value Idn of the drive current Id required for the stationary movement of the sensor head 31 with the threshold Id0. An example of the setting of the threshold Id0 includes any value in a range of one and a half times to three times the maximum value of the stationary value Idn.

In addition, in the present embodiment, the reference position P0 is set to the same position as the stop position PL for Large size located at an outermost position in the CD direction among the above-mentioned three stop positions PS, PM, PL, or is set to a position located to the outer side of the outermost stop position. For example, as shown in FIG. 3D, the reference position P0 is set to a position located outside of the stop position PL for Large size. Accordingly, when the product size is changed, it is possible to effectively avoid interferences such as contact of the sensor head 31 with the continuous sheet 3 during the movement of the sensor head 31 to the reference position P0 (see FIGS. 4A and 4B). As a result, troubles preventing the sensor head 31 from reaching the reference position P0 by getting caught by the continuous sheet 3, and troubles by such a sensor head 31 being caught causing tearing or folding damage to the continuous sheet 3 can be obviated.

Here, regarding the positional relationship of the above-mentioned reference position P0, it is more preferable that the reference position P0 is set to the stop position PL located at the outermost position in the CD direction, that is, the same position as the stop position PL for Large size. With this configuration, the positioning accuracy of the sensor head 31 at the stop position PL for Large size can be increased. The details are as follows.

Figure 7:
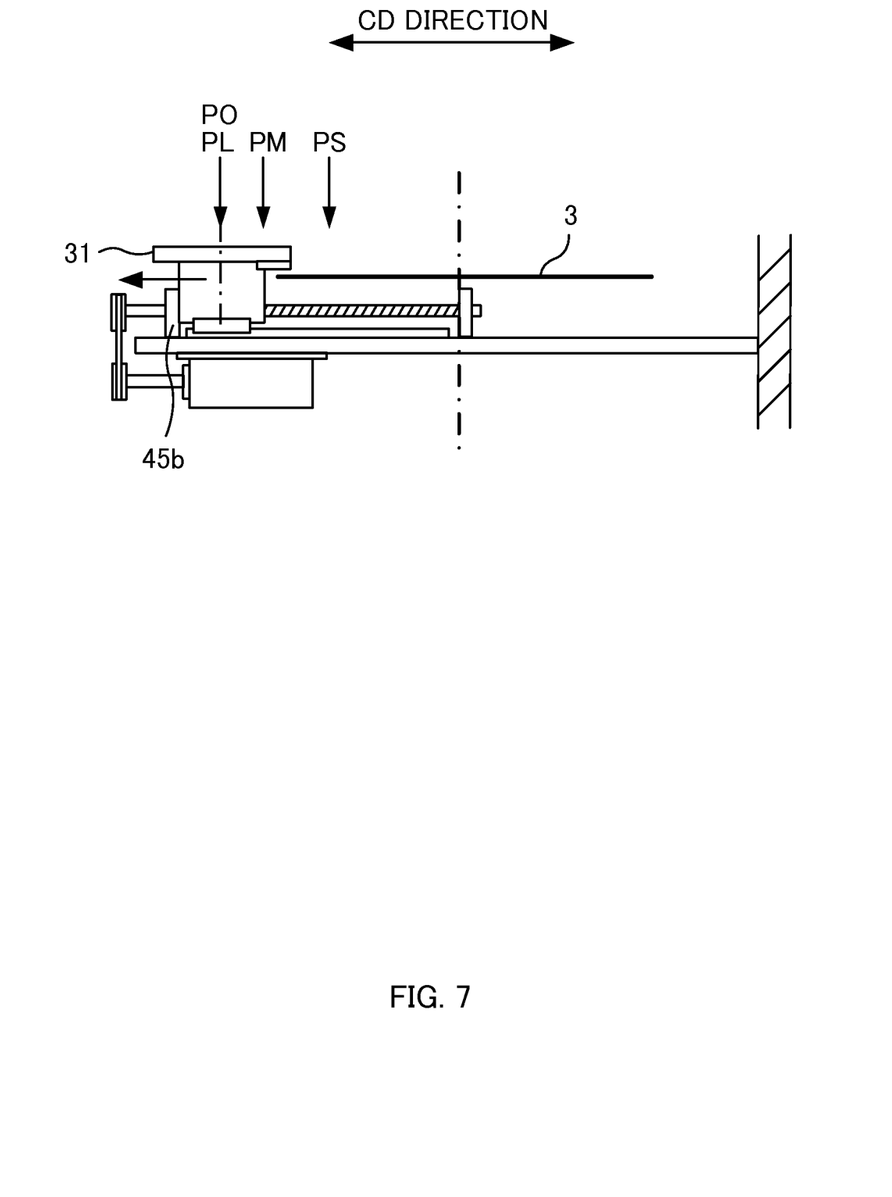
FIG. 7 is an explanatory view of a desirable positional relationship between the reference position P0 and the stop position PL for Large size.

First, as shown in FIG. 7, when the product size is changed to Large size, the sensor head 31 is once moved to the reference position P0 in order to perform the zero-reset of the count value associated with the movement of the sensor head 31. After that, the sensor head 31 is moved to the stop position PL for Large size. However, by matching the stop position PL for Large size with the reference position P0 as mentioned above, the sensor head 31 will be positioned at the stop position PL for Large size without moving from the reference position P0 at all. As a result, the sensor head 31 can be accurately positioned at the stop position PL without any error effects associated with the movement from the reference position P0 to the stop position PL for Large size.

Furthermore, as shown in the examples of FIGS. 2B and 2C, when the edge sensor 30 is provided only at one side (left side in the figures) in the CD direction, it is desirable that the edge sensor 30 is provided at the other side (left side in the figures) in the CD direction, that is, the opposite side in the CD direction to the side where the panel board 11 is provided. Accordingly, since the detecting section 33 of the sensor head 31 associated with the edge sensor 30, the drive mechanism 43 of the moving mechanism 40 and the like are arranged at positions away from the panel board 11 in the CD direction, the panel board 11 will not interfere with these devices when performing maintenance and inspection thereof. Also, workspace can be easily secured, and maintenance can be performed easier as well.

Figure 8A:
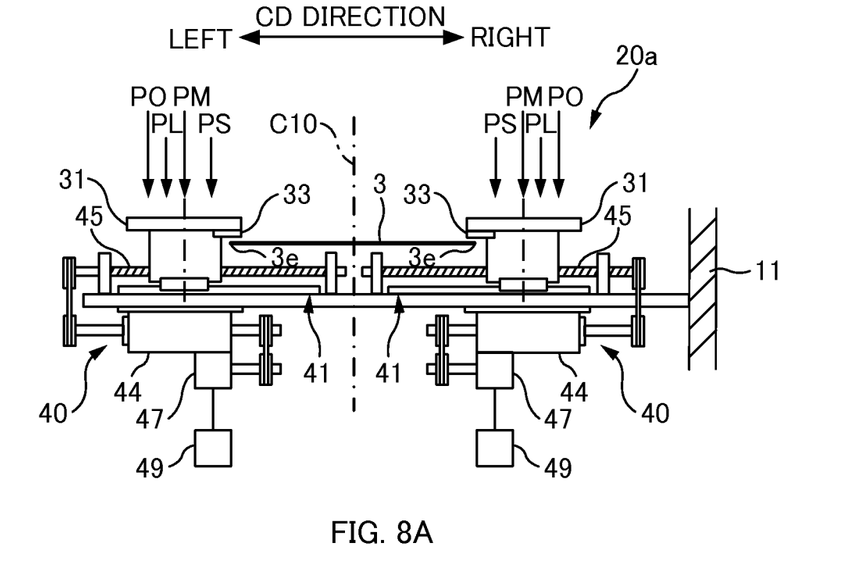
FIG. 8A is an explanatory view of a meandering correction apparatus 20a of a first modified example.

FIG. 8A is an explanatory view of a meandering correction apparatus 20*a* of a first modified example. In the above-mentioned embodiment, the sensor head 31 is provided only at one side in the CD direction. And this was used for correcting the meandering by detecting only the position of the edge 3*e* of the continuous sheet 3 at one side in the CD direction of the sheet (FIGS. 3A to 3C).

In this regard, in the first modified example in FIG. 8A, the sensor heads 31, 31 are provided on both sides in the CD direction. In response to this, the moving mechanisms 40, 40 are also provided on both sides in the CD direction respectively. Due to this, the stop positions PS, PM, PL for Small, Medium, and Large sizes and the reference position P0 are also set for each sensor head 31, 31.

A detection signal S30L of the left side detecting section and a detection signal S30R of the right side detecting section 33 in the CD direction are output to the first controller 59 in real time. In the first controller 59, an arithmetic average of these detection signals S30L and S30R is determined in real time to generate one signal S30$a$ (=(S30L+S30R)/2). The first controller 59 controls the oil hydraulic cylinder 56 in the meandering correcting section 50 based on the signal S30$a$.

At that time, regarding both left and right sides detection signals S30L and S30R, the relationship between the right and left moving direction of the position of the edge 3*e* and the increase and decrease direction of the values indicated by the detection signals S30L and S30R is adapted between both the left side detection signal S30L and the right side detection signal S30R, for example, in such a manner that the values indicated by the detection signals S30L and S30R increase when the position of the edge 3e of the continuous sheet 3 is moved to the left, and the values indicated by the detection signals S30L and S30R decrease when the position thereof is moved to the right.

With such a configuration, even when the width of the continuous sheet 3 is changed in the same continuous sheet 3, the amount of meandering of the continuous sheet 3 can be accurately figured out without being influenced by this width change. The details are as follows.

As shown in the above-mentioned embodiment in FIG. 3B, in the case that only the position of the edge 3e at one side in the CD direction is detected, even if the continuous sheet 3 is not meandering, that is, even if the central position of the continuous sheet 3 in the width direction of the sheet corresponds with the central position C10 of the manufacturing line 10, when the width of the continuous sheet 3 is widened or narrowed, the position of the edge 3e at one side is also changed in the CD direction by an amount by which the width of the continuous sheet 3 has been widened or narrowed. Therefore, even when the continuous sheet 3 is not meandering, the first controller 59 responds to this and controls the oil hydraulic cylinder 56 in the meandering correcting section 50 so as to correct the position of the above-mentioned edge 3e. Thereby, there is a risk of inducing unnecessary meandering.

In contrast, as shown in the first modified example of FIG. 8A, if the arithmetic average of the detection signals S30L and S30R on both sides is determined, the influence caused by the change of the width of the continuous sheet 3 is compensated by the calculation of the arithmetic average. In other words, the signal S30a generated by calculating the arithmetic average purely indicates the change of the center position in the width direction of the continuous sheet 3. Therefore, in the continuous sheet 3, even when the width thereof is varied, the amount of meandering of the continuous sheet 3 can be accurately figured out without being influenced at all by this width variation.

Figure 8B:
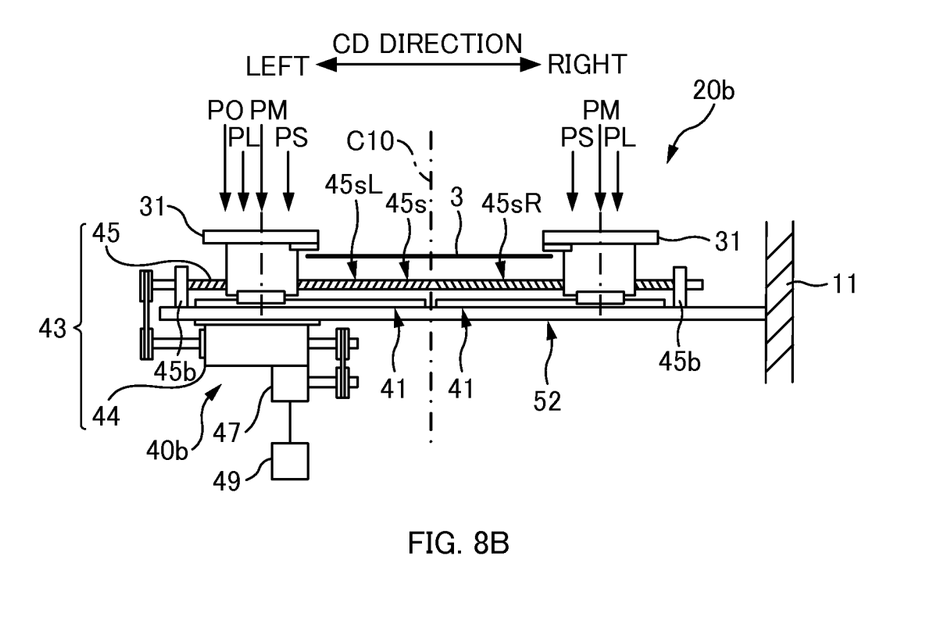
FIG. 8B is an explanatory view of a meandering correction apparatus 20b of a second modified example.

FIG. 8B is an explanatory view of a meandering correction apparatus 20b of a second modified example. The second modified example is different from the above-mentioned first modified example that the moving mechanism 40 which moves the sensor head 31 is not provided at each sensor head 31, 31, but generally only one moving mechanism is provided. That is, the right and left two sensor heads 31, 31 generally share one moving mechanism 40b. Note that, the other configurations are generally the same as those in the first modified example.

Specifically, although guide members 41, 41 of the moving mechanism 40b are provided at each sensor head 31, 31 respectively, the drive mechanism 43 of the sensor head 31, rotary encoder 47, second controller 49 and the like are shared.

More specifically, first, the entire length of the screw shaft 45s of the feed screw mechanism 45 associated with the drive mechanism 43 is longer than the width of the continuous sheet 3 for Large size, and the same screw shaft 45s is disposed across the continuous sheet 3 in the CD direction over substantially the entire length in the CD direction. The helical groove on the outer circumferential surface of the screw shaft 45s is formed so that the screw thread of the left half part 45sL and that of the right half part 45sR are in a reversed relation with the central position C10 of the manufacturing line 10 as a boundary therebetween. Therefore, when the screw shaft 45s rotates in the normal direction (for example, clockwise), each of the sensor heads 31, 31 is moved toward the outside in the CD direction (a direction in which the sensor heads 31, 31 are separated from each other). On the other hand, when the screw shaft 45s rotates in the reverse direction (for example, counterclockwise), each of the sensor heads 31, 31 is moved toward the inside in the CD direction (a direction in which the sensor heads 31, 31 approach each other).

Since the number of the screw shafts 45s is one as mentioned above, naturally, the number of the motors 44 that drive the screw shaft 45s is one as well, and the number of the rotary encoders 47 that measure the amount of rotation of the screw shaft 45s is one as well. Moreover, the number of the second controllers 49 that control the motor 44 is one as well.

Bearing members 45b, 45b by which the screw shaft 45s is rotatably supported on the fixed pedestal 52 are, for example, provided at both end portions in the CD direction. One (left side in FIG. 8B) of these bearing members 45b, 45b is arranged with respect to the above-mentioned reference position P0. Therefore, this left side bearing member 45b serves as a member that forms the above-mentioned limit position for physical movement. More specifically, the reference position P0 is detected by the left side sensor head 31 abutting the left side bearing member 45b, and both of the right and left sensor heads 31, 31 are aligned at each stop positions PS, PM, PL based on the above single reference position P0.

With such a second modified example, since the number of components such as the motor 44 and the rotary encoder 47 can be reduced compared to that in the above-mentioned first modified example, the configuration of the apparatus can be simplified. In this regard, the second modified example is superior to the first modified example.

However, in terms of accuracy in positioning to the stop positions PS, PM, PL, the first modified example is superior to the second modified example. More specifically, as mentioned above, in the case of the first modified example in FIG. 8A, both sensor heads 31, 31 are positioned at each stop position PM, PM based on each corresponding reference position P0, P0, respectively. On the other hand, in the case of the second modified example in FIG. 8B, both sensor heads 31, 31 are positioned at each stop position PM, PM at once based on the reference position P0 of the left side sensor head 31 which is one of the right and left sensor heads 31, 31. That is, the positioning of the right side sensor head 31, which is the other sensor head 31, to the stop position PM is also performed based on the reference position P0 of the left side sensor head which is the one of the sensor head 31. Therefore, regarding the right side sensor head 31 which is the other sensor head 31, it becomes impossible to position the other sensor head 31 at the stop position PM based on the optimal reference position P0 for the other sensor head 31. Thus, the positioning accuracy of the other sensor head 31 at the stop position PM becomes low. Accordingly, in terms of positioning accuracy, it can be considered that the first modified example is more desirable.

Other Embodiments

While the embodiments according to the invention have been described above, the invention is not limited to the embodiments and can be altered as described below.

In the foregoing embodiment, as an example of the absorbent article, disposable diapers worn by a wearer to absorb excreted fluid thereof has been given. However, the invention is not limited thereto as long as the article absorbs excreted fluid such as urine, menstrual blood, or the like. For example, sanitary napkins or pet sheets that absorb excreted fluid of pets may also be used.

In the foregoing embodiment, the rotary encoder 47 described as an example of the signal output section is a type which generates a number of pulses being substantially proportional to the amount of rotation (rotation angle) of the input shaft 47*a*. However, the invention is not limited thereto. For example, a type which outputs a digital value being proportional to the amount of rotation of the input shaft 47*a* may be used. In this case, although the counter circuit is not necessary, the second controller 49 is operated in the following manner to move the sensor head 31 to each stop position PS, PM, and PL.

First, as shown in FIG. 4B, when the sensor head 31 reaches the reference position P0, a digital value that is output at the time of reaching is recorded in a memory of the second controller 49 as a reference value. Further, in the memory of the second controller 49, each corresponding value that corresponds to the moving distance from the reference position P0 to each stop position PS, PM, and PL is recorded in advance in a form of a digital value for each stop position PS, PM, and PL. Accordingly, the second controller 49 controls the motor 44 so that the sensor head 31 is moved in one direction and stopped when a deviation between the digital value and the reference value matches with the corresponding value. Thereby, as shown in FIG. 4C, the sensor head 31 is positioned at each stop position PS, PM, and PL.

In the foregoing embodiment, the product size (size specification) was described as an example of "specifications". However, as long as the concept is such that each dimension in the width direction of the continuous sheet 3 is different from each other, the invention is not limited thereto.

REFERENCE SIGNS LIST

3 continuous sheet, 3S continuous sheet of Small size,
3M continuous sheet of Medium size, 3L continuous sheet of Large size,
3*e* edge, 3*r* sheet roll,
10 manufacturing line, 10*b* foundation,
11 panel board (plate member), 11*a* vertical surface, 13 reel device, 14 processing unit,
20 meandering correction apparatus, 20*a* meandering correction apparatus, 20*b* meandering correction apparatus,
30 edge sensor (sensor), 31 sensor head, 33 detecting section,
40 moving mechanism, 40*b* moving mechanism,
41 guide member, 41*a* rail, 41*b* slider,
43 drive mechanism, 44 motor, 44*a* drive rotational shaft,
44*p* pulley, 44*t* timing belt,
45 feed screw mechanism, 45*b* bearing member,
45*s* screw shaft, 45*s*L left half part, 45*s*R right half part,
47 rotary encoder (signal output section),
47*a* input shaft, 47*p* pulley, 47*t* timing belt,
49 second controller (controller),
50 meandering correcting section, 52 fixed pedestal, 54 oscillating base, 56 oil hydraulic cylinder,
58 transport roll, 58*b* bearing member,
59 second controller,
P0 reference position, PS stop position for Small size,
PM stop position for Medium size, PL stop position for Large size,
C10 central position, C54 fixed shaft, C58 shaft core,
S30 detection signal

The invention claimed is:

1. A meandering correction apparatus arranged in a manufacturing line of an absorbent article for correcting meandering of a continuous sheet, which is associated with the absorbent article and is continuously transported in a transporting direction, wherein the continuous sheet is selected, to be transported, from among a plurality of continuous sheets having specifications with different dimensions in a width direction of the manufacturing line, said apparatus comprising:
   a sensor including a detecting section that is configured to detect a position of an edge of the continuous sheet in the width direction in a state in which the detecting section is stopped at a stop position among a plurality of stop positions each set in the width direction for a corresponding specification among the specifications,
   a meandering correcting section configured to correct meandering of the continuous sheet based on a detection signal of the position of the edge which is output from the sensor, and
   a moving mechanism including
      a motor that is configured to move the detecting section in the width direction,
      a signal output section that is configured to output a signal in accordance with the movement of the detecting section in the width direction, and
      a controller that is configured to control the motor based on the signal output from the signal output section,
   wherein
   the controller is configured to
      set a corresponding value that corresponds to a moving distance of the detecting section from a predetermined reference position to each of the plurality of stop positions, the predetermined reference position being a limit position for physical movement of the detecting section in the width direction,
      cause the motor to move the detecting section to the stop position based on the corresponding value and the signal output from the signal output section, and
      detect that the detecting section reaches the reference position based on a drive current value of the motor,
   the predetermined reference position is
      located at a same position as an outermost stop position in the width direction among the stop positions, or
      located outside of the outermost stop position in the width direction,
   in a case where a first continuous sheet with a first specification is transported, the controller is configured to move the detecting section from the predetermined reference position in the width direction to a first stop position among the stop positions, the first stop position being set for the first specification, and
   in a case where the first continuous sheet is changed to a second continuous sheet with a second specification different from the first specification, the controller is configured to
      move the detecting section outwardly in the width direction toward the predetermined reference position, then
      detect that the detecting section reaches the predetermined reference position based on the drive current value of the motor, and then
      move the detecting section inwardly in the width direction from the predetermined reference position to a second stop position among the stop positions, the second stop position being set for the second specification.

2. The apparatus according to claim 1, wherein
   the sensor includes another detecting section, and the detecting sections of the sensor are arranged on two opposing sides of the manufacturing line in the width direction.

3. The apparatus according to claim 2, wherein
the moving mechanism is provided to each of the detecting sections, and
the predetermined reference position and the stop positions are set to the each of the detecting sections.

4. The apparatus according to claim 3, wherein the controller is configured to move the detecting sections to the corresponding stop positions independently from each other.

5. The apparatus according to claim 1, wherein
the meandering correction apparatus is supported by a vertically standing plate member at one side of the manufacturing line in the width direction, and
the sensor is provided only at another side of the manufacturing line, said another side opposing said one side in the width direction.

6. The apparatus according to claim 1, wherein the reference position is the same as the outermost stop position in the width direction.

* * * * *